United States Patent [19]
Ardelt

[11] Patent Number: 5,728,805
[45] Date of Patent: *Mar. 17, 1998

[54] PHARMACEUTICALS AND METHOD FOR MAKING THEM

[75] Inventor: Wojciech J. Ardelt, New City, N.Y.

[73] Assignee: Alfacell Corp., Bloomfield, N.J.

[*] Notice: The term of this patent shall not extend beyond the expiration date of Pat. No. 5,529,715.

[21] Appl. No.: 467,955

[22] Filed: Jun. 6, 1995

Related U.S. Application Data

[63] Continuation-in-part of Ser. No. 283,970, Aug. 1, 1994, Pat. No. 5,559,212, which is a continuation of Ser. No. 814,332, Feb. 3, 1992, abandoned, which is a continuation of Ser. No. 436,141, Nov. 13, 1989, abandoned, which is a continuation-in-part of Ser. No. 178,118, Apr. 6, 1988, Pat. No. 4,882,421.

[51] Int. Cl.$^6$ .................. C07K 14/46; A61K 38/17
[52] U.S. Cl. .................. 530/350; 530/416; 530/427; 514/12; 514/21
[58] Field of Search .................. 530/350, 416, 530/427; 435/815; 424/94.61

[56] References Cited

U.S. PATENT DOCUMENTS

| | | | |
|---|---|---|---|
| 4,374,061 | 2/1983 | Bing | 525/54.1 |
| 4,882,421 | 11/1989 | Shogen et al. | 530/350 |
| 5,529,775 | 6/1996 | Mikulski et al. | 424/94.6 |
| 5,540,925 | 7/1996 | Mikulski et al. | 424/94.6 |
| 5,559,212 | 9/1996 | Ardelt | 530/350 |
| 5,595,734 | 1/1997 | Mikulski et al. | 424/94.6 |

FOREIGN PATENT DOCUMENTS

| | | |
|---|---|---|
| WO 89/09606 | 10/1989 | WIPO. |
| WO 91/07435 | 5/1991 | WIPO. |
| WO 94/03197 | 2/1994 | WIPO. |

OTHER PUBLICATIONS

Schloen et al. Pyruvate kinase isozymes in adult tissues and eggs of *Rana pipiens*. Archives of Biochemistry and Biophysics. vol. 164, No. 1, pp. 254–265, Sep. 1974.

Kawauchi et al. Agglutinins of frog eggs: a new class of proteins causing preferential agglutination of tumor cells. Experientia. vol. 31, No. 3, pp. 364–365, Oct. 17, 1974.

Nitta et al. Isolation and characterization of *Rana catesbeiana* lectin and demonstration of the lectin–binding glycoprotein of rodent and human tumor cell membranes. Cancer Research. vol. 47, pp. 4877–4883, Sep. 15, 1987.

Shibuya et al. Stabilization and enhancement of primary cytostatic factor (CSF) by ATP and NaF in amphibian egg cytosols. Developmental Biology. vol. 129, No. 1, Abstract, Sep. 1988.

Shibuya et al. Molecular characteristics of cytostatic factors in amphibian egg cytosols. Development. vol. 106, No. 4, Abstract, 1989.

Sue et al. Purification, characterization and anti–tumor activity of *Rana–nigromaculata* lectin. Yakugaku Zasshi. vol. 100, No. 7, pp. 706–712, 1980.

Kamiya et al. Amino acid sequence of a lectin from Japanese frog (*Rana japonica*) eggs. Journal of Biochemistry. vol. 108, No. 1, pp. 139–143, 1990.

Titani et al. Amino acid sequence of sialic acid binding lectin from frog (*Rana catesbeiana*) eggs. Biochemistry. vol. 26, pp. 2189–2201, 1987.

Ardelt et al. Amino acid sequence of an anti–tumor protein from *Rana pipiens* oocytes and early embryos: homology to pancreatic ribonucleases. The Journal of Biological Chemistry. vol. 256, No. 1, pp. 245–251, Jan. 5, 1991.

Nitta et al. Primary structure of a ribonuclease from bullfrog (*Rana catesbeiana*) liver. Journal of Biochemistry. vol. 106, pp. 729–735, 1989.

*Primary Examiner*—Stephen Walsh
*Assistant Examiner*—Brian Lathrop

[57] ABSTRACT

*Rana pipiens* eggs are subjected to mechanical processing in the presence of a weakly acidic buffer to produce an extract. The extract is subjected to ion-exchange chromatography and size-exclusion chromatography. Two pharmaceuticals resulting from these steps have activity against certain cancer cells. The amino acid sequences and compositions of two preferred embodiments are disclosed.

5 Claims, 9 Drawing Sheets

Figure 8

```
  1   2   3   4   5   6   7   8   9  10
<Glu-Asp-Trp-Leu-Thr-Phe-Gln-Lys-Lys-His- 11                                  20
Ile-Thr-Asn-Thr-Arg-Asp-Val-Asp-Cys-Asp- 21                                  30
Asn-Ile-Met-Ser-Thr-Asn-Leu-Phe-His-Cys- 31                                  40
Lys-Asp-Lys-Asn-Thr-Phe-Ile-Tyr-Ser-Arg- 41                                  50
Pro-Glu-Pro-Val-Lys-Ala-Ile-Cys-Lys-Gly- 51                                  60
Ile-Ile-Ala-Ser-Lys-Asn-Val-Leu-Thr-Thr- 61                                  70
Ser-Glu-Phe-Tyr-Leu-Ser-Asp-Cys-Asn-Val- 71                                  80
Thr-Ser-Arg-Pro-Cys-Lys-Tyr-Lys-Leu-Lys- 81                                  90
Lys-Ser-Thr-Asn-Lys-Phe-Cys-Val-Thr-Cys- 91                                 100
Glu-Asn-Gln-Ala-Pro-Val-His-Phe-Val-Gly- 101         104
Val-Gly-Ser-Cys
```

Figure 9

```
  1    2    3    4    5    6    7    8    9   10
<Glu-Asp-Trp-Leu-Thr-Phe-Gln-Lys-Lys-His- 11                                        20
Val-Thr-Asn-Thr-Arg-Asp-Val-Asp-Cys-Asn- 21                                        30
Asn-Ile-Met-Ser-Thr-Asn-Leu-Phe-His-Cys- 31                                        40
Lys-Asp-Lys-Asn-Thr-Phe-Ile-Tyr-Ser-Arg- 41                                        50
Pro-Glu-Pro-Val-Lys-Ala-Ile-Cys-Lys-Gly- 51                                        60
Ile-Ile-Ala-Ser-Lys-Asn-Val-Leu-Thr-Thr- 61                                        70
Ser-Glu-Phe-Tyr-Leu-Ser-Asp-Cys-Asn-Val- 71                                        80
Thr-Ser-Arg-Pro-Cys-Lys-Tyr-Lys-Leu-Lys- 81                                        90
Lys-Ser-Thr-Asn-Lys-Phe-Cys-Val-Thr-Cys- 91                                       100
Glu-Asn-Gln-Ala-Pro-Val-His-Phe-Val-Gly- 101           104
Val-Gly-Arg-Cys
```

PHARMACEUTICALS AND METHOD FOR MAKING THEM

CROSS-REFERENCE TO RELATED APPLICATIONS

This application is a continuation-in-part of commonly owned patent application of Ardelt, application Ser. No. 08/283,970 filed Aug. 1, 1994 now U.S. Pat. No. 5,559,212, which is a continuation of application Ser. No. 07/814,332, filed Feb. 3, 1992 and now abandoned, which is a continuation of application Ser. No. 07/436,141, filed Nov. 13, 1989 and now abandoned, which is a continuation-in-part of commonly-owned application of Shogen et al., application Ser. No. 07/178,118, filed Apr. 6, 1988 and now U.S. Pat. No. 4,882,421. The entire disclosures of these patent applications, including the drawings thereof, are hereby incorporated into this application by reference.

BACKGROUND OF THE INVENTION

The invention relates to pharmaceuticals, and more particularly relates to pharmaceuticals for use in treating tumors in humans.

At present, tumors are treated either by chemotherapy, radiotherapy or surgery. Each of these therapies has disadvantages.

It would be advantageous to avoid the disadvantages of chemotherapy, radiotherapy and surgery.

One object of the invention is to provide a pharmaceutical therapy for tumors in humans.

Another object is to provide such a therapy that has less disadvantageous side effects than those of other known therapies.

A further object is to provide such a therapy for use with more than one type of tumor.

Still a further object is, in general, to improve on known therapies for treatment of tumors in humans.

In accordance with the invention, there are provided two preferred embodiments of a pharmaceutical for treatment of tumors in humans. In both embodiments, the pharmaceutical is a pure protein having a molecular weight of approximately 12,000 and a characteristic high isoelectric point. The two embodiments have similar, but not identical, amino acid compositions. Advantageously although not necessarily, the embodiments are derived from frog eggs; in a preferred embodiment, the pharmaceutical is derived from eggs of the Rana pipiens frog. The derivation is carried out by mechanical processing, ion-exchange chromatography and size-exclusion chromatography.

U.S. Pat. No. 4,882,421 describes a method for making a pharmaceutical that has anti-tumor activity. In the above-referenced abandoned application Ser. No. 07/436,141, filed Nov. 13, 1989 and subsequently-filed continuations thereof, that pharmaceutical is described with reference to its amino acid sequence and composition; the therein described pharmaceutical is the herein-described and herein-claimed first preferred embodiment.

Abandoned application Ser. No. 07/436,141, filed Nov. 13, 1989 and subsequently-filed continuations thereof teach that a large protein peak (containing antiproliferative/cytotoxic activity) coming off an ion-exchange chromatography column is isolated, and also teach the specific description of that active protein peak. Another protein coming off the ion-exchange chromatography column has now been purified to a state of homogeneity and characterized; this second protein is the second preferred embodiment described and claimed herein. Since this second preferred embodiment is eluted from the column later than the first preferred embodiment, the second preferred embodiment contains material that is more basic. Tests have shown that this second preferred embodiment also possesses bioactivity against certain cancer cell lines. The two herein-described and claimed preferred embodiments are closely related proteins that have slightly different amino acid sequences and the second protein is more basic than the first one.

The first preferred embodiment is presently being used in clinical trials and it has been necessary to produce comparatively large quantities of this material. A preferred methodology—which is believed to be suitable, in scaled-up form, for production of the first preferred embodiment in commercial-size lots—for so doing is set forth below. The second preferred embodiment has only been produced in small quantities and no easily scaled-up methodology for producing it presently exists.

BRIEF DESCRIPTION OF THE DRAWINGS

The invention will be better understood with reference to the following illustrative and non-limiting drawings, in which:

FIG. 8 shows the amino acid sequence of a pharmaceutical in accordance with SEQ ID NO:1, the first preferred embodiment of the invention; and FIG. 9 shows the amino acid sequence of a pharmaceutical in accordance with SEQ ID NO:2, the second preferred embodiment of the invention.

DETAILED DESCRIPTION OF PREFERRED EMBODIMENTS

I. Manufacturing Methodology

A. Accumulating Eggs of *Rana pipiens*

Figure 1:
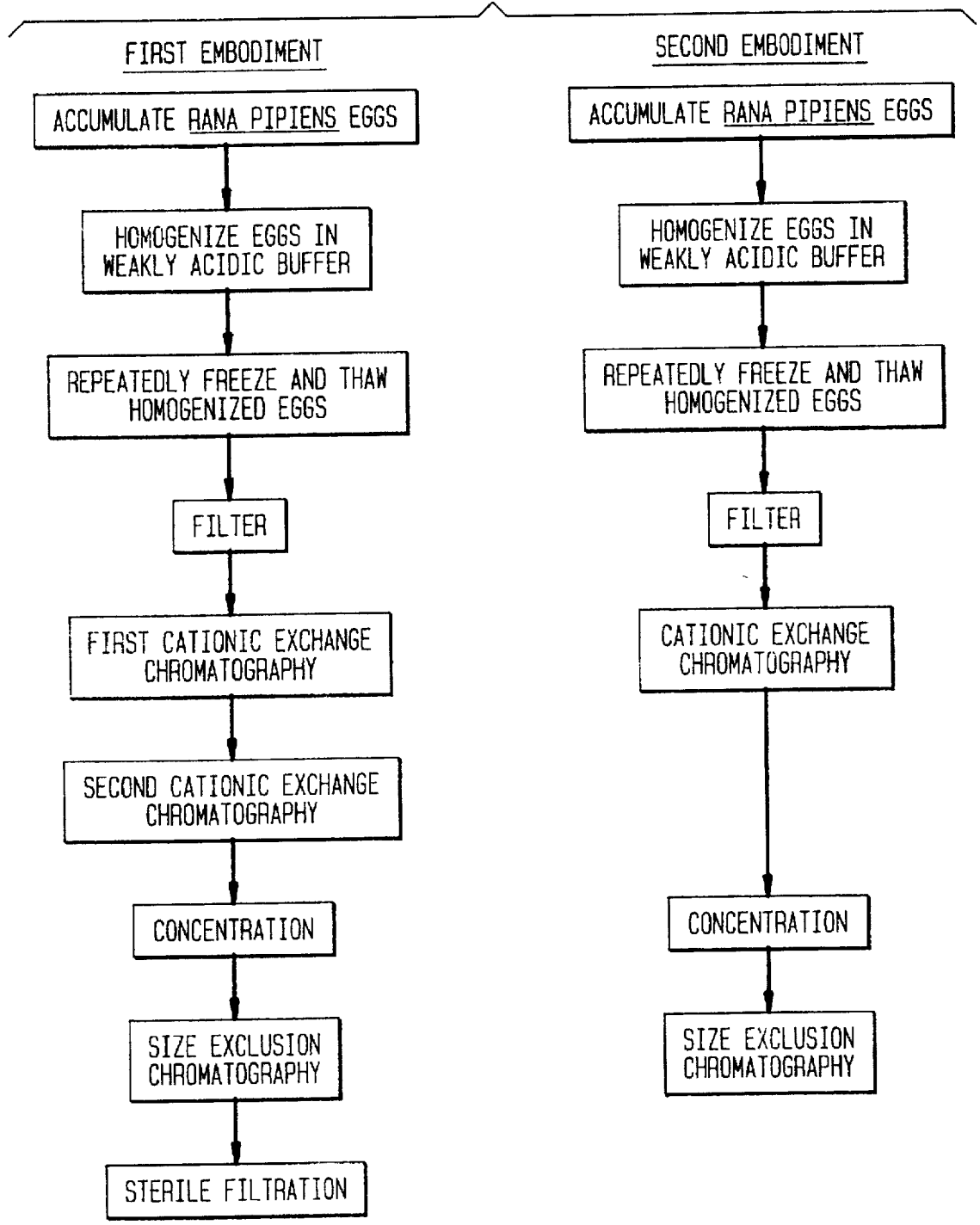
FIG. 1 is a flow chart showing how the preferred embodiments are produced, and showing a preferred method in accordance with the invention.

In accordance with the preferred embodiment of the invention, *Rana pipiens* eggs are obtained from female *Rana pipiens* during the months of April through August (when the female *Rana pipiens* ovulates spontaneously). The eggs are then scraped into containers and stored in frozen form at −15° C. to −20° C. This storage is not essential for the practice of the invention; it is preferred only when it is convenient to carry out subsequent processing in batches. Typically, subsequent steps are carried out using batches of eggs weighing about 16–21 kg.

B. Mechanical Processing of the Eggs

If the eggs have been frozen, they are thawed by any method that does not overheat them. The thawed or never-frozen eggs are then homogenized in the presence of a weakly acidic buffer and subjected to a series of freeze-thaw cycles.

In the preferred embodiment, the eggs are mixed, at room temperature, with 0.15M sodium acetate (pH 5.0) using two parts of buffer by weight for one like weight of eggs. The buffer need not be sodium acetate but should be acidic; sodium acetate is used because, in the preferred embodiment, SP-Sepharose FF chromatography is carried out and sodium acetate is a good buffer within a pH range of 4–5.8 (in which range SP-Sepharose exchange columns are efficient), and a weakly acidic buffer increases the capacity of the column and produces better separation. Homogenization is carried out in a Waring Blender until all eggs have been disrupted as observed visually, but a Waring Blender is not required and any sanitary method for accomplishing thorough homogenization can be used. Homogenization is complete when the suspension appears homogenous with no visual sign of intact eggs. In accordance with the preferred embodiment, homogenization lasts for 5 minutes at high speed. Aliquots (0.5 kg–1.0 kg) are homogenized, bottled and frozen separately.

All aliquots of homogenate are then thawed overnight at ambient temperature; approximately 15–17 hours is preferred. The bottles are then shaken manually and the homogenate is refrozen and stored at −20° C.±10° C. for 24 hours. The thawing and refreezing cycle is repeated four more times in succession. At the end of the fifth cycle, the bottles of homogenate are stored at −20° C.±10° C.

The freeze-thaw cycles reduce the viscosity of the homogenate, thereby reducing clogging of the chromatographic column (described below). The use of freeze-thaw cycles, while effective for its purpose, requires substantial time and increases the duration of the manufacturing process; it may be possible to accomplish the freeze-thaw cycles in a lyophilizer to save time.

All of the freeze/thaw-treated homogenate aliquots are thawed overnight at ambient temperature, in the unopened storage containers. The thawed freeze/thaw-treated homogenate is then filtered, in successive portions, through a plastic net in a Process Plastic Column (Pharmacia, PP 252/30, or equivalent) using a peristaltic pump. The insoluble residue is pressed against the bottom of the filter with the flow adaptor. The filtrates are collected. The insoluble residue is resuspended in 0.15M sodium acetate (pH 5.0) in the column segment, stirred manually, and filtered. The quantity of buffer solution used in this step is about one third of the initial homogenate weight. The insoluble residue is then removed and discarded before processing the next portion of thawed homogenate as described above. The filtrates from all homogenate portions are combined.

The DEAE Sepharose filter (25.2×1–2 cm, set up in a Pharmacia, PP 252/30 column segment) is washed with 3 kg of 0.15M sodium acetate (pH 5.0). To remove debris that could clog the columns in the below-described processing steps, the combined filtrates from the previous step are passed twice through the DEAE Sepharose filter, using a peristaltic pump. The filtrate is collected in a pre-weighed container, and then two separate volumes of 0.15M sodium acetate (pH 5.0) (1.0 kg each) are passed through the filter. All filtrates from these steps are combined in a 15–30 gallon tank. The combined filtrate solution is stirred with a mechanical stirrer for 5 to 10 minutes and weighed.

If the stirred combined filtrate solution is to be further processed within 48 hours, it is stored at 2° C.–8° C. Otherwise, if further processing is to take place more than 48 hours later, the stirred combined filtrate solution is frozen and stored at −20° C.±10° C.

As will be described in more detail below, the stirred combined filtrate solution is an intermediate from which the first and second preferred embodiments of the invention can be extracted. To produce the first preferred embodiment of the invention, the stirred combined filtrate solution is subjected to two steps of cationic exchange chromatography, a step of concentration, and a step of size exclusion chromatography (in the order listed). To produce the second preferred embodiment of the invention, the stirred combined filtrate solution is subjected to a step of cationic exchange chromatography, a step of concentration, and a step of size exclusion chromatography. Steps C1, D1, E1 and F1 below describe production of the first preferred embodiment of the invention, and steps C2, D2 and E2 describe production of the second preferred embodiment of the invention.

C1. First Cationic Exchange Chromatography

In the first cationic exchange chromatography that is described below, the two active proteins and other basic molecules bind to the exchange resin and are retained in the column. Most other components are eluted from the column when the column is initially loaded. Thereafter, the active protein is eluted using a stepwise gradient of sodium chloride in 0.15M sodium acetate buffer, pH 5.0. The result is a material that is essentially free of endotoxin.

To determine when the eluate contains active protein, the eluate is continuously monitored for absorbance of 280 nm ultraviolet light (hereinafter, "280 nm UV"). This is because proteins are highly absorbant of light at that wavelength and absorbance of 280 nm UV is therefore a good indication that active protein is coming off the column.

A Pharmacia Process Plastic Column (PP113/60, or equivalent) is packed with a SP Sepharose FF (Pharmacia) resin to obtain a 11.3 cm×30–40 cm bed (3.0 L to 4.0 L). This column has a DEAE Sepharose FF pre-filter in 0.15M sodium acetate (pH 5.0). The DEAE Sepharose FF is packed into a Pharmacia Process Plastic Column (PP 252/15, or equivalent) and has a bed size of 25.2×1 to 2 cm). The pre-filter and process column are equilibrated with 0.15M sodium acetate (pH 5.0) until the column effluent is pH 5.0±0.1 and 280 nm UV absorbance shows a flat baseline.

The stirred combined filtrate solution produced at the end of step B. above is brought to room temperature. Then, it is loaded onto the column through the pre-filter using a peristaltic pump with a linear flow rate of 50–75 cm/h and subjected to cationic exchange chromatography in the column.

Figure 2:
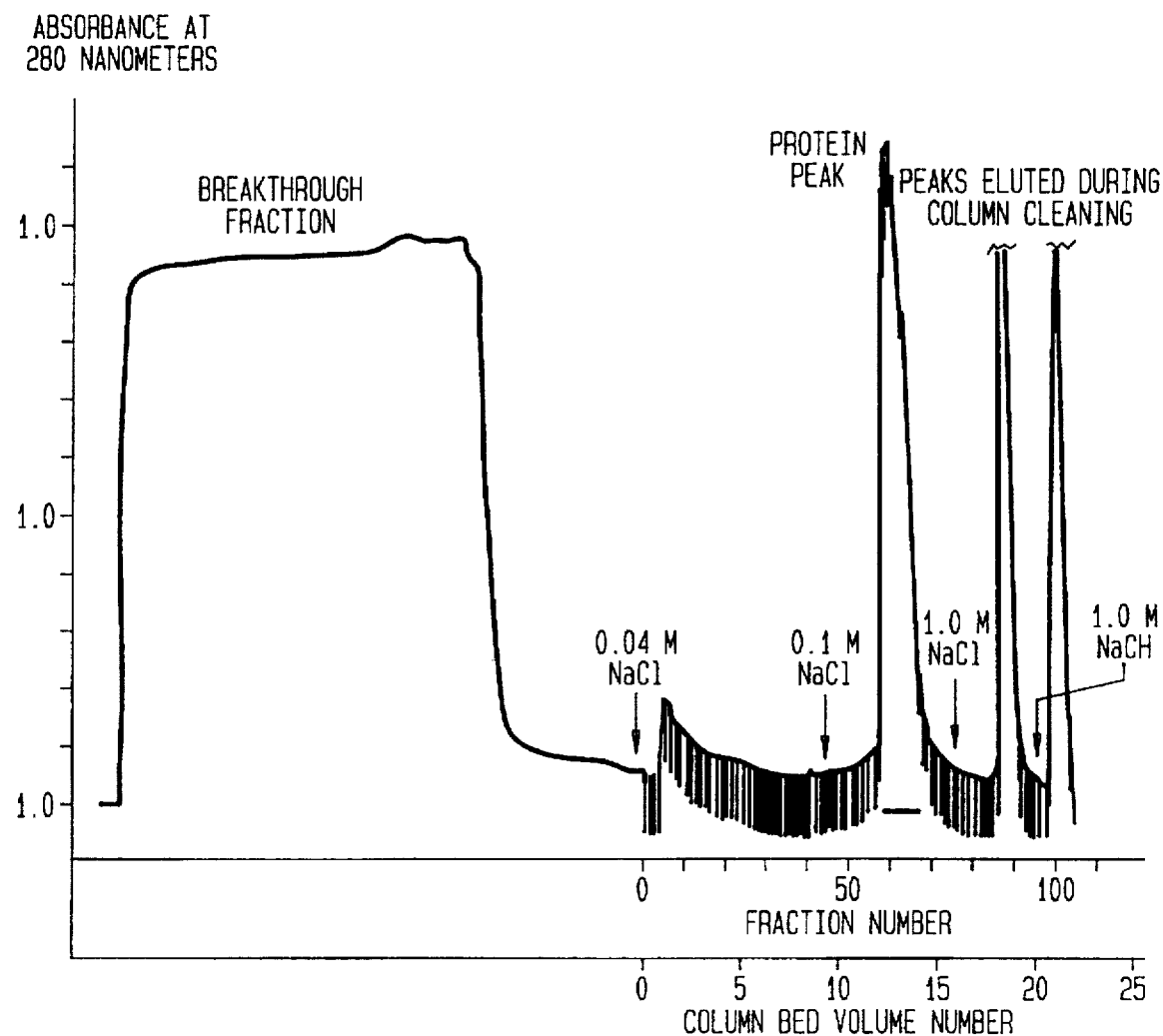
FIG. 2 shows an exemplary chromatographic record of the results of the first cationic exchange chromatography in accordance with the preferred method for producing a pharmaceutical in accordance with the first preferred embodiment of the invention.

The initial "breakthrough fraction" eluted during column loading (see FIG. 2) is discarded. When column loading is complete. 0.15M sodium acetate (pH 5.0) is passed through the column until 280 nm UV absorbance is close to the baseline. The effluent is discarded and the pre-filter is disconnected.

Seven to ten column bed volumes of 0.04M NaCl in 0.15M sodium acetate buffer, pH 5.0 are then passed through the column while 280 nm UV absorbance is continuously monitored. The eluate (components that are weakly bound to the cationic exchange resin) is discarded until the onset of a second rise in 280 nm UV absorbance.

At this point, the buffer containing 0.04M NaCl is replaced with the buffer containing 0.1M NaCl. At least two column volumes of the buffer are passed through the column, and the peak eluted by 0.1M sodium chloride in the buffer is collected while 280 nm UV absorbance is at the large peak in FIG. 2 labelled Protein Peak. The eluate, which contains the first of the two active proteins (i.e. the first preferred embodiment of the invention) in partially purified form, is collected in a sanitized container.

D1. Second Cationic Exchange Chromatography

In the second cationic exchange chromatography step described below, the conditions are exactly the same as in the first cationic exchange chromatography step described at C. above. Thus, 0.04M sodium chloride in 0.15M sodium acetate buffer is run first (this time, at least 15 bed volumes are passed through the column) and the first active protein (i.e. the first preferred embodiment of the invention) is eluted using 0.1M sodium chloride in the buffer once the absorbance of 280 nm UV begins to rise.

The second cationic exchange chromatography step, as well as each subsequent manufacturing step, is carried out in a clean room. All buffer solutions are prepared with Sterile Water for Injection, USP, and filtered through sterile 0.22 µm, Sterivex-GS membrane filters (Millipore Corp., or equivalent) before use.

A Pharmacia BioProcess Glass Column (BPG 100/750, or equivalent) is packed with SP Sepharose FF (Pharmacia) to obtain a 10 cm×30–40 cm (2.35 L to 3.1 L) resin bed. The column is equilibrated in a 0.15M sodium acetate buffer, pH 5.0.

The partially purified active protein eluted at the end of the previous cationic chromatography step described in step C. above is diluted with an equal volume of Sterile Water for Injection, USP, and loaded onto the column using a peristaltic pump operating at 50 to 75 cm/hr.

Figure 3:
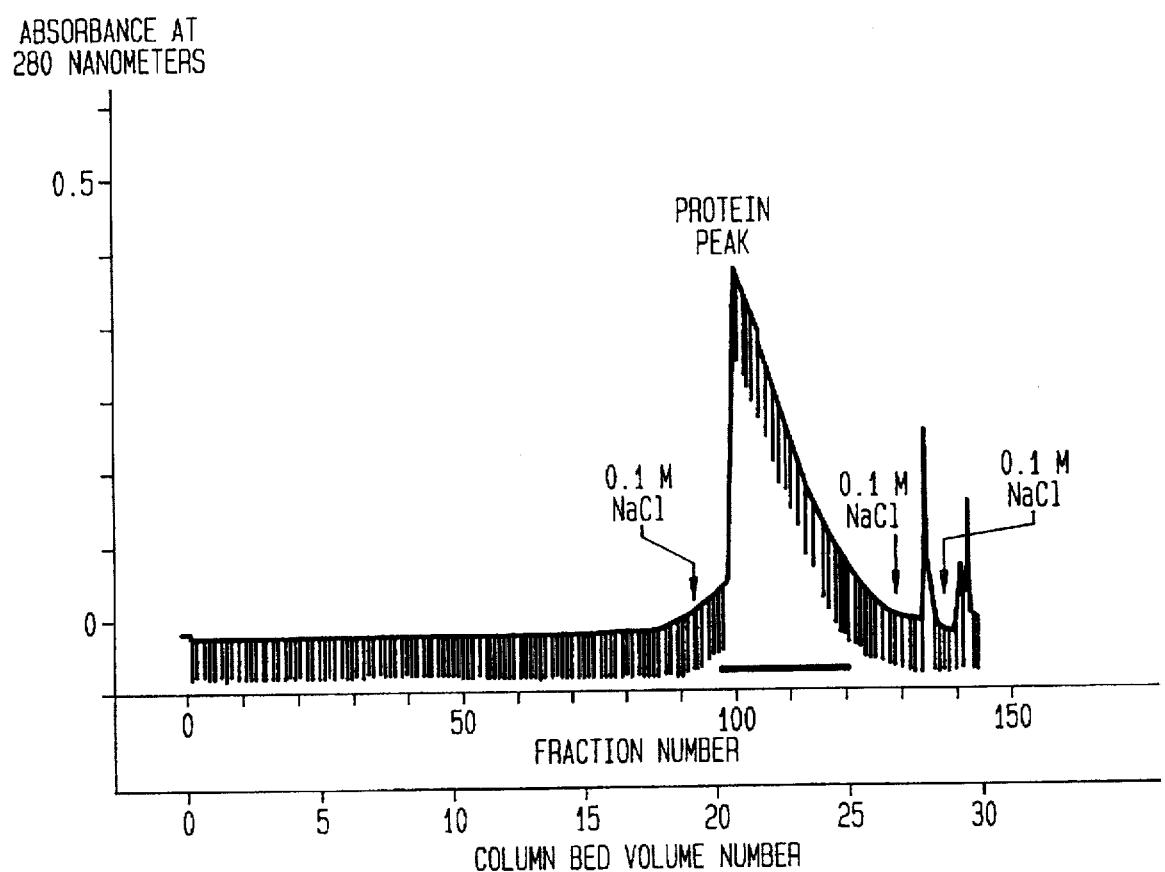
FIG. 3 shows an exemplary chromatographic record of the results of the second cationic exchange chromatography in accordance with the preferred method for producing a pharmaceutical in accordance with the first preferred embodiment of the invention.

Once the partially purified active protein has been loaded onto the column, at least 15 column bed volumes of 0.04M NaCl in 0.15M sodium acetate buffer, pH 5.0 are passed through the column. This continues until absorbance of 280 nm UV rises above the baseline. When this happens, the buffer is changed to 0.1M NaCl in 0.15M sodium acetate buffer, pH 5.0, and at least two column bed volumes of NaCl buffer are passed through the column. The effluent (located under the peak in FIG. 3 which is labelled Protein Peak), which contains the active protein, is collected in a sanitized container. E1. Concentration by Chromatography In this step, the protein containing effluent is concentrated by SP Sepharose FF chromatography. A Pharmacia BioProcess Glass Column (BPG 100/500, or equivalent) is packed with SP Sepharose FF resin (Pharmacia) to obtain a 10 cm×7–10 cm bed. A peristaltic pump operating at 50–75 cm/hr is used for loading and elution of the column, and as in the previous chromatography steps the absorbance of 280 nm UV light is continuously monitored.

The column is equilibrated with 0.15M sodium acetate (pH 5.0) until the column effluent is pH 5.0±0.1 and the 280 nm UV absorbance shows a flat baseline.

The protein-containing effluent produced at the end of step D. above is diluted with an equal volume of Sterile Water for Injection, USP, and is loaded onto the column. The absorbance of 280 nm UV is continuously monitored. Once the column loading is complete, the column is washed with one column volume of Sterile Water for Injection, USP, to remove excess sodium acetate buffer.

1M NaCl is then run through the column. 280 nm UV absorbance is continuously monitored, and the peak of the first active protein (i.e. the first preferred embodiment of the invention) is collected in a sanitized container. This peak is labelled Protein Peak in FIG. 4.

F1. Purification by Size Exclusion Chromatography

Size exclusion chromatography is carried out on the concentrated active protein produced at the end of step E. above. Although the protein recovered from the previous step is highly purified, it still contains small amounts of other molecules. These molecules have the same isoelectric point as does the first preferred embodiment, or isoelectric points that are very similar thereto. Consequently, these molecules were not removed during the previous steps of cationic exchange chromatography. However, these molecules have different molecular weights than does the first preferred embodiment of the invention, and they are removed by size exclusion chromatography during this step.

Two columns are used in tandem; each is a Pharmacia BioProcess Glass Column (BPG 200/950 or equivalent). (Tandem columns were chosen because this is an expedient way of obtaining a column bed of an appropriate size. It is not necessary for the invention.) Each column is packed with Sephacryl S-100 High Resolution resin (Pharmacia) to form a 20 cm×50–60 cm resin bed (17–20 L each column). A peristaltic pump adjusted to a flow rate of 5–10 cm/h is used to feed materials to the columns, and the eluate's absorbance of 280 nm UV light is continuously monitored.

The columns are equilibrated with at least two column bed volumes of 0.075M ammonium bicarbonate in Sterile Water for Injection, USP. Concentrated active protein produced at the end of step E. above is loaded onto the columns, followed by 0.075M ammonium bicarbonate in Sterile Water for Injection, USP. The 280 nm UV absorbance of the eluate is continuously monitored.

Figure 5:
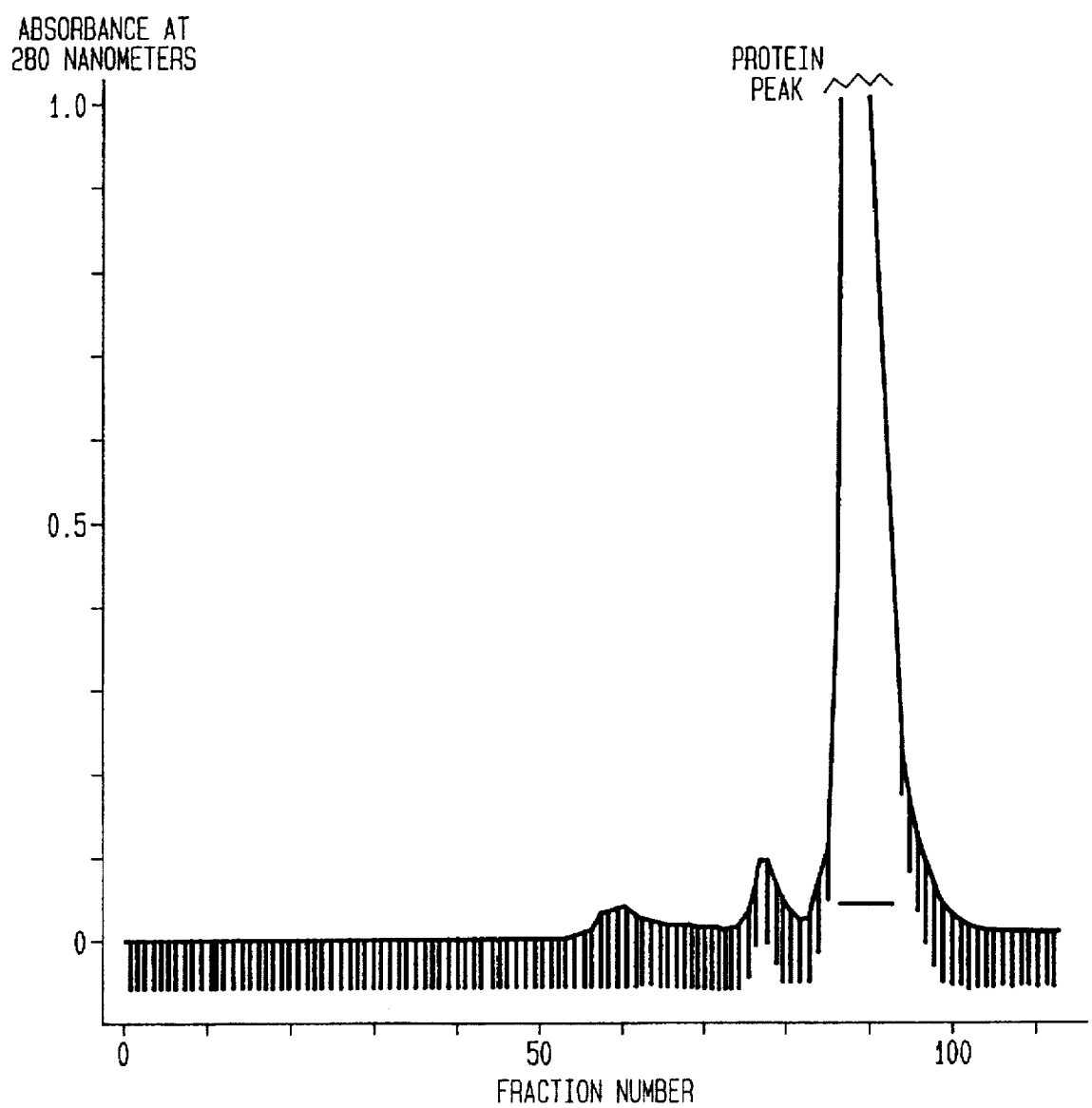
FIG. 5 shows an exemplary chromatographic record of the results of a size exclusion chromatography in accordance with the preferred method, whereby a pharmaceutical in accordance with the first preferred embodiment of the invention is finally purified.

Molecules of higher molecular weight than the active protein elute from the columns before the active protein does. These peaks are discarded. Fractions of the main peak containing the active protein (these are located under the peak labelled Protein Peak in FIG. 5) are collected in sanitized bottles. Aliquots (0.05 mL to 0.1 mL) of the fractions under the ascending and descending shoulders of the peak are tested for purity. Based on the results obtained, fractions containing pure protein are combined with the main portion of the peak in a sanitized, high density polyethylene or polypropylene container.

The resulting pure protein-containing solution is filtered through a sterile 0.22 µm. Sterivax-GS (Millipore Corp., or equivalent) membrane filter into a sterile container. This filtrate is a sublot of the active protein.

C2. Cationic Exchange Chromatography

Figure 6:
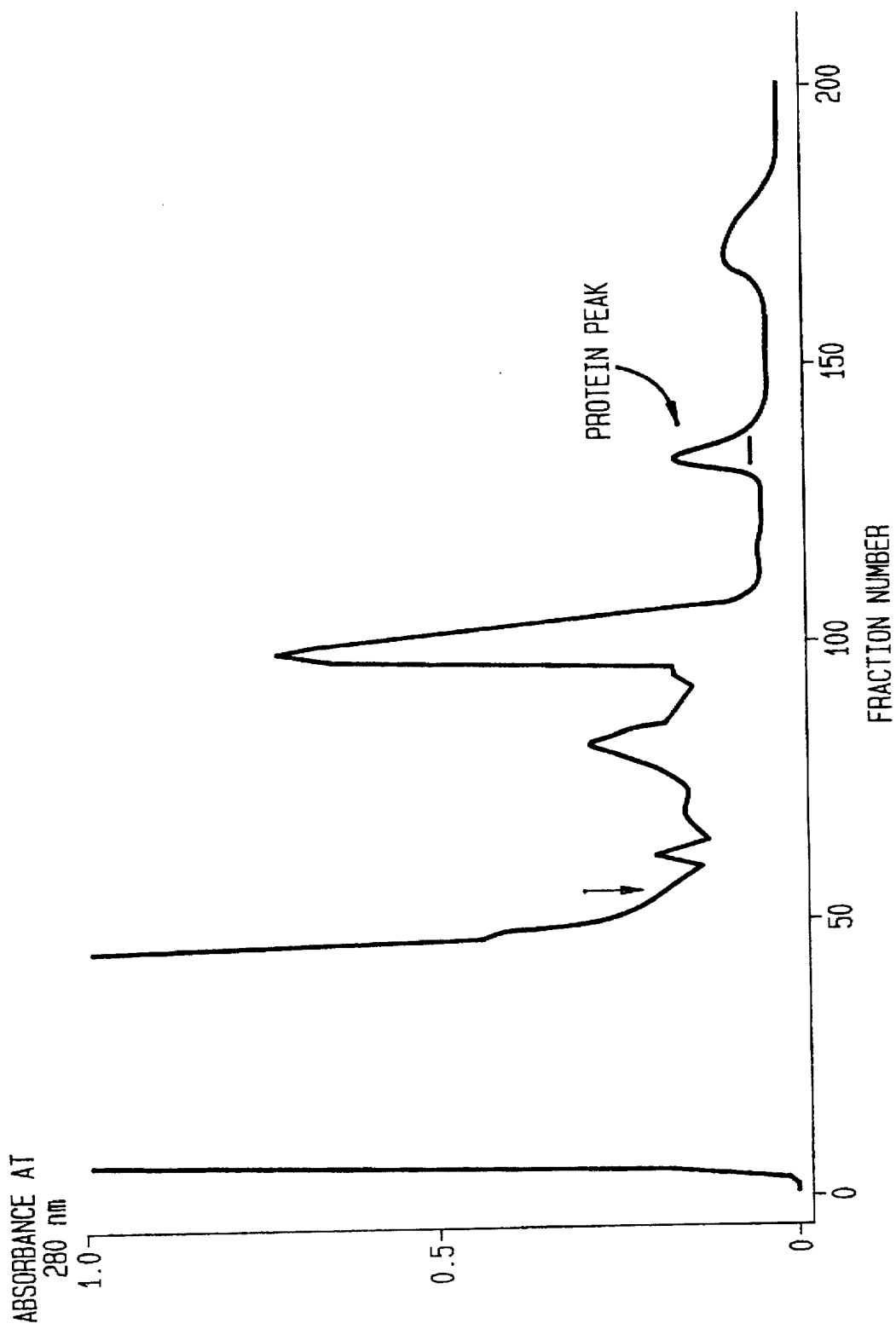
FIG. 6 shows an exemplary chromatographic record of the results of a cationic exchange chromatography for producing a pharmaceutical in accordance with the second preferred embodiment of the invention.

A chromatographic column is packed with SP Sepharose FF resin to form a bed that is 2.5 cm in diameter and 7.2 cm long. The column is equilibrated in 0.15M sodium acetate buffer. The stirred combined filtrate solution produced at the end of step B. above is loaded onto the column at a flow rate of 50 mL/hour. The chromatography is continuously monitored by measuring the absorption of 280 nm UV light, and fractions of 5.85 mL each are automatically collected. The breakthrough fraction (ending at approximately fraction 51) is discarded. The column is then developed with a continuous sodium chloride gradient (0M–0.45M) made in the equilibrating buffer. The peak in FIG. 6 indicated by a bar and labelled Protein Peak contains the second preferred embodiment of the invention, and all fractions under this peak are collected.

D2. Concentration

The fractions collected at the end of step C2. above are then concentrated as in step E1 above. A Pharmacia Bio- Process Glass Column (BPG 100/500, or equivalent) is packed with SP Sepharose FF resin (Pharmacia) to obtain a 2.5 cm×1.3 cm bed. A peristaltic pump operating at 50–75 cm/hr is used for loading and elution of the column, and the absorbance of 280 nm UV light is continuously monitored.

The column is equilibrated with 0.15M sodium acetate (pH 5.0) until the column effluent is pH 5.0±0.1 and the 280 nm UV absorbance shows a flat baseline.

The fractions collected at the end of step C2. above are diluted with an equal volume of water and loaded onto the column. The absorbance of 280 nm UV is continuously monitored. Once the column loading is complete, the column is washed with one column volume of water to remove excess sodium acetate buffer.

Figure 4:
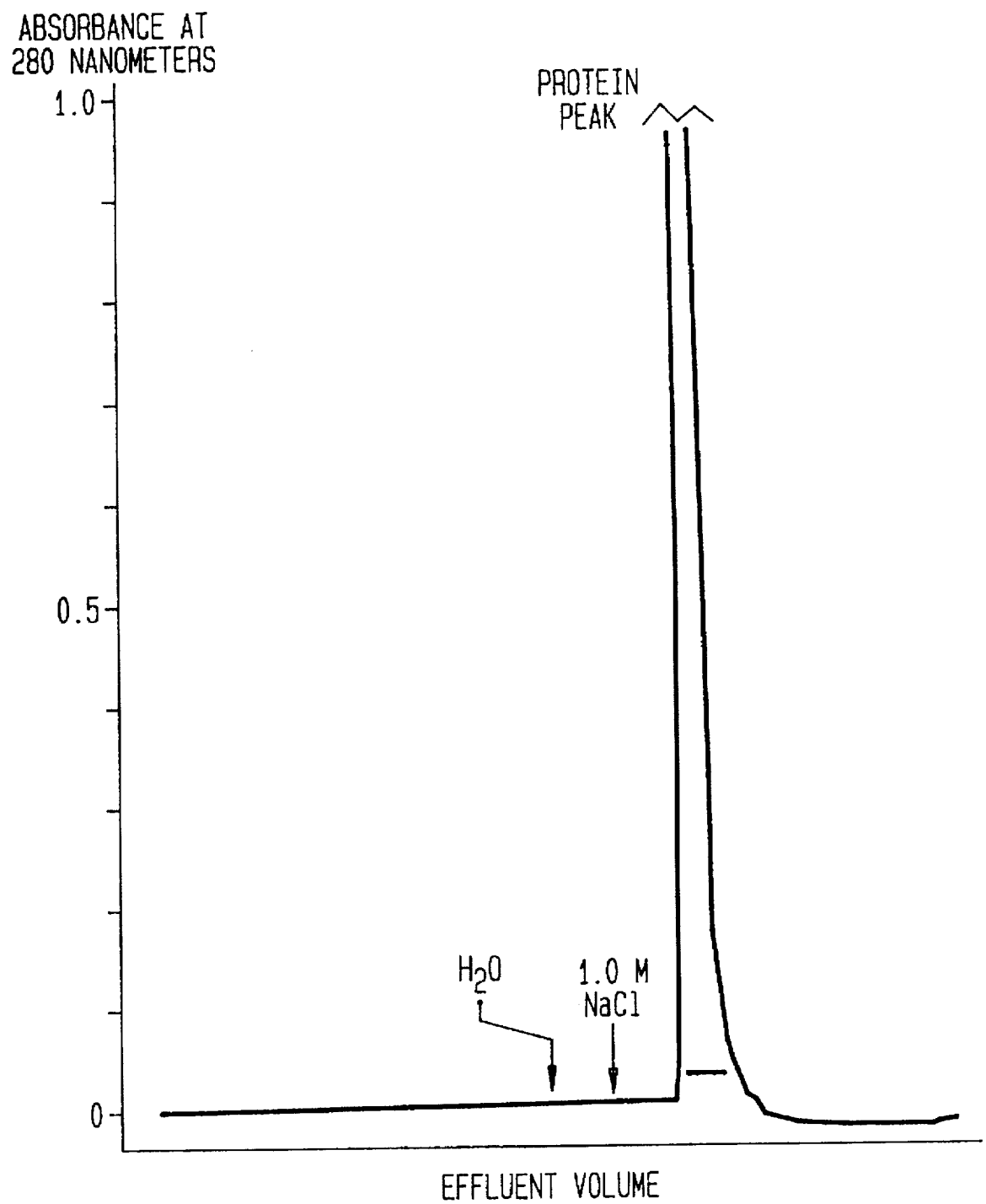
FIG. 4 shows an exemplary chromatographic record of the results of a third cationic exchange chromatography in accordance with the preferred method for manufacturing pharmaceuticals in accordance with the first and second preferred embodiments of the invention, whereby the active protein is concentrated.

1M NaCl is then run through the column. 280 nm UV absorbance is continuously monitored, and the peak in FIG. 4 labelled Protein Peak (i.e. the second preferred embodiment of the invention) is collected in a sanitized container.

E2. Size Exclusion Chromatography

Figure 7:
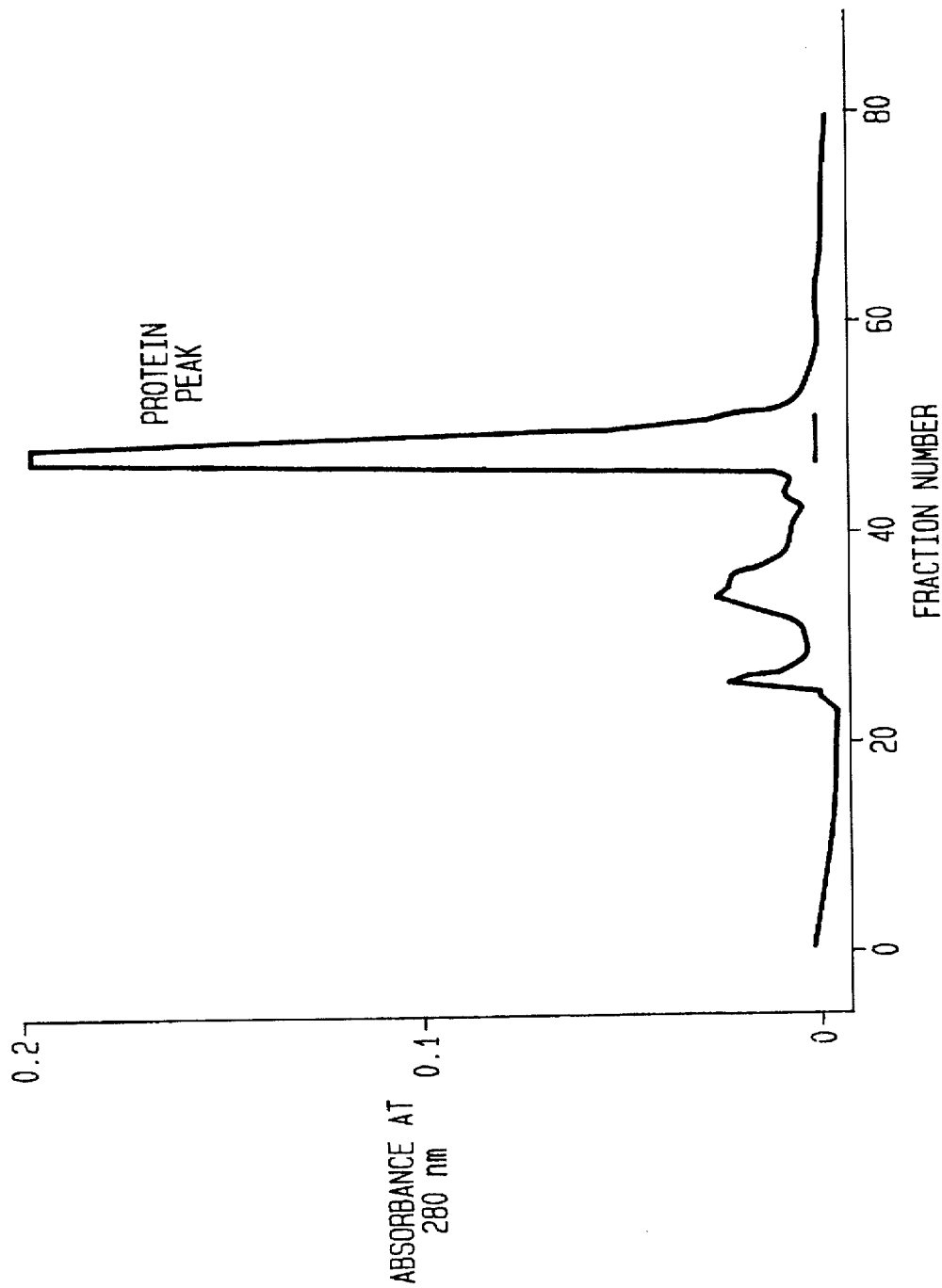
FIG. 7 shows an exemplary chromatographic record of the results of a size exclusion chromatography for finally purifying a pharmaceutical in accordance with the second preferred embodiment of the invention.

The fractions collected at the end of step D2. above are chromatographed in a column which is packed with Sephacryl S-100 High Resolution resin (Pharmacia) to form a 2.5 cm×46 cm bed, using 0.075M ammonium bicarbonate in water. Fractions are automatically collected. Fractions under the main peak (this peak is labelled Protein Peak in FIG. 7) were collected; these collected fractions are the second preferred embodiment of the invention in a purified state.

II. Bioactivity of the Preferred Embodiments

Confirmatory in vitro and in vivo animal data show that a pharmaceutical in accordance with the first preferred embodiment of the invention is active against human submaxillary epidermoid carcinoma A-253 cells and human ovarian adenocarcinoma NIH-OVCAR-3 cells. This first preferred embodiment has also shown activity against human leukemic HL-60 cells, human COLO 320 DM cells originally isolated from colon adenocarcinoma, human LOX melanoma, and human lung squamous carcinoma HT-520 cells.

Published articles reporting the activity of a pharmaceutical in accordance with the first preferred embodiment of the invention appear at:

Cell Tissue Kinet. (1988) 21, 169–182

Br. J. Cancer (1992) 66, 304–310.

Int. J. Oncol. (1992) 1, 779–785.

In vitro data show that the second preferred embodiment of the pharmaceutical is active against human submaxillary epidermoid carcinoma A-253 cells and human bladder carcinoma T-24 cells.

CHEMICAL ANALYSIS AND COMPOSITION OF PREFERRED EMBODIMENTS

The preferred embodiments of the invention have been well characterized chemically. While the embodiments are proteins isolated from Rana pipiens, it is believed that they may be produced using genetic engineering techniques, as long as the end result has the following chemistry and structure:

Both embodiments are a pure proteins (i.e. homogeneous, as established by standard tests that are used to assay the homogeneity of proteins). Calculation of the molecular weights based upon the below listed amino acid sequences indicates that the molecular weights should be 11,835 in the case of the first preferred embodiment; in the case of the second preferred embodiment, 11,890. As determined by mass spectrometry, the molecular weight of the first preferred embodiment is approximately 12,000, and the molecular weight of the second preferred embodiment as determined by mass spectrometry is expected to be the same.

Both preferred embodiments have an isoelectric point pI that is between 9.5 and 10; by calculation from the known sequences, the isoelectric point pI of the first preferred embodiment is 9.70 and the isoelectric point pI of the second preferred embodiment is 9.94. Both also have a blocked amino terminal group and are essentially free of carbohydrates (as determined by anthrone and orcinol methods).

The preferred embodiments of the invention have the following characteristics:

Amino Acid Analysis—First Preferred Embodiment

| AMINO ACID RESIDUE | MOL % (24 HOUR ACID HYDROLYSIS) | |
|---|---|---|
| Aspartic acid/Asparagine | 13.99 | |
| Threonine | 9.30 | (Note 1) |
| Serine | 7.78 | |
| Glutamic acid/Glutamine | 6.10 | |
| Proline | 4.36 | |
| Glycine | 3.09 | |
| Alanine | 3.09 | |
| Cystine/2 | 6.92 | (Note 1) |
| Valine | 8.20 | |
| Methionine | 0.85 | (Note 1) |
| Isoleucine | 4.86 | (Note 2) |
| Leucine | 5.22 | |
| Tyrosine | 2.96 | |
| Phenylalanine | 6.05 | |
| Histidine | 2.88 | |
| Lysine | 11.62 | |
| Arginine | 2.70 | |
| Tryptophan | Not Determined | (Note 3) |
| Approximate Total | 99.97% | |

Note 1: Threonine, cystine/2 and methionine are partially destroyed during hydrolysis and this value is uncorrected for such partial destruction.
Note 2: This value is uncorrected for incomplete hydrolysis.
Note 3: Tryptophan cannot be detected in acid hydrolysis of proteins because it is destroyed and is consequently shown as Not Determined. However, analysis of the ultraviolet spectrum revealed the presence of one tryptophan residue per molecule.

Amino Acid Analysis—Second Preferred Embodiment

| AMINO ACID RESIDUE | RESIDUES PER MOLECULE | |
|---|---|---|
| Aspartic acid/Asparagine | 13.63 | |
| Threonine | 8.82 | (Note 1) |
| Serine | 6.18 | (Note 1) |
| Glutamic acid/Glutamine | 6.21 | |
| Proline | 4.23 | |
| Glycine | 3.21 | |
| Alanine | 2.99 | |
| Cystine/2 | 7.42 | |
| Valine | 8.76 | |
| Methionine | 1.15 | |
| Isoleucine | 4.37 | (Note 2) |
| Leucine | 5.29 | |
| Tyrosine | 3.08 | |
| Phenylalanine | 5.88 | |
| Histidine | 3.06 | |
| Lysine | 11.84 | |
| Arginine | 3.79 | |
| Tryptophan | Not Determined | (Note 3) |
| Approximate Total | 99.91% | |

Note 1: This value is corrected for partial destruction during hydrolysis.
Note 2: This value is corrected for incomplete hydrolysis.
Note 3: Tryptophan cannot be detected in acid hydrolysis of proteins because it is destroyed and is consequently shown as Not Determined. However, the sequence clearly shows the presence of one tryptophan residue per molecule.

Amino Acid Composition—First Preferred Embodiment (as calculated from amino acid sequence)

| AMINO ACID | NUMBER OF RESIDUES PER MOLECULE OF MATERIAL |
|---|---|
| Aspartic acid | 6 |
| Asparagine | 8 |
| Threonine | 10 |
| Serine | 8 |
| Glutamic acid | 3 |
| Pyroglutamic acid | 1 |
| Glutamine | 2 |
| Proline | 4 |
| Glycine | 3 |
| Alanine | 3 |
| Cystine/2 | 8 |
| Valine | 8 |
| Methionine | 1 |
| Isoleucine | 6 |
| Leucine | 5 |
| Tyrosine | 3 |
| Phenylalanine | 6 |
| Histidine | 3 |
| Lysine | 12 |
| Arginine | 3 |
| Tryptophan | 1 |
| Total | 104 |

Amino Acid Composition—Second Preferred Embodiment (as calculated from amino acid sequence)

| AMINO ACID | NUMBER OF RESIDUES PER MOLECULE OF MATERIAL |
|---|---|
| Aspartic acid | 5 |
| Asparagine | 9 |
| Threonine | 10 |
| Serine | 7 |
| Glutamic acid | 3 |
| Pyroglutamic acid | 1 |
| Glutamine | 2 |
| Proline | 4 |
| Glycine | 3 |
| Alanine | 3 |
| Cystine/2 | 8 |
| Valine | 9 |
| Methionine | 1 |
| Isoleucine | 5 |
| Leucine | 5 |
| Tyrosine | 3 |
| Phenylalanine | 6 |
| Histidine | 3 |
| Lysine | 12 |
| Arginine | 4 |
| Tryptophan | 1 |
| Total | 104 |

The preferred embodiments of the invention have been sequenced. As is shown below, the total length of the sequence in both instances is 104 residues. The N-terminus of the protein is pyroglutamic acid (<Glu). This is a cyclized derivative of glutamic acid that is devoid of the free amino group necessary for direct sequencing and that therefore "blocks" the N-terminus of the protein.

The first preferred embodiment of the invention, SEQ ID NO:1, has the following amino acid sequence:

```
 1    2    3    4    5    6    7    8    9   10
<Glu—Asp—Trp—Leu—Thr—Phe—Gln—Lys—Lys—His—
11                                            20
Ile— Thr— Asn—Thr— Arg—Asp—Val—Asp—Cys—Asp—
21                                            30
Asn—Ile — Met—Ser—Thr—Asn—Leu—Phe—His—Cys—
31                                            40
Lys—Asp—Lys—Asn—Thr—Phe—Ile— Tyr—Ser— Arg—
41                                            50
Pro— Glu— Pro— Val— Lys—Ala—Ile— Cys—Lys—Gly—
51                                            60
Ile— Ile— Ala—Ser— Lys—Asn—Val—Leu—Thr—Thr—
61                                            70
Ser— Glu— Phe—Tyr— Leu—Ser— Asp—Cys—Asn—Val—
71                                            80
Thr— Ser— Arg—Pro— Cys—Lys—Tyr—Lys—Leu—Lys—
81                                            90
Lys—Ser— Thr—Asn—Lys—Phe—Cys—Val—Thr—Cys—
91                                           100
Glu—Asn—Gln—Ala— Pro—Val—His—Phe—Val—Gly—
101        104
Val—Gly—Ser—Cys—
```

The second preferred embodiment of the invention, SEQ ID NO:2, has the following amino acid sequence:

```
 1    2    3    4    5    6    7    8    9   10
<Glu—Asp—Trp—Leu—Thr—Phe—Gln—Lys—Lys—His—
11                                            20
Val—Thr— Asn—Thr— Arg—Asp—Val—Asp—Cys—Asn—
21                                            30
Asn—Ile— Met—Ser— Thr—Asn—Leu—Phe—His—Cys—
31                                            40
Lys—Asp—Lys—Asn—Thr—Phe—Ile— Tyr—Ser— Arg—
41                                            50
Pro— Glu— Pro— Val— Lys—Ala—Ile— Cys—Lys—Gly—
51                                            60
Ile— Ile— Ala—Ser— Lys—Asn—Val—Leu—Thr—Thr—
61                                            70
Ser— Glu— Phe—Tyr— Leu—Ser— Asp—Cys—Asn—Val—
71                                            80
Thr— Ser— Arg—Pro— Cys—Lys—Tyr—Lys—Leu—Lys—
81                                            90
Lys—Ser— Thr—Asn—Lys—Phe—Cys—Val—Thr—Cys—
91                                           100
Glu—Asn—Gln—Ala— Pro—Val—His—Phe—Val—Gly—
101        104
Val—Gly—Arg—Cys—
```

Although two preferred embodiments have been described above, the scope of the invention is limited only by the following claims:

I claim:

1. A purified protein having the amino acid sequence shown in SEQ ID NO:2.

2. A purified variant of the protein having the amino acid sequence shown in SEQ ID NO:1, wherein said variant has anti-tumor activity in humans, and wherein said variant differs from the protein of SEQ ID NO:1 solely by substitution of one or more of the amino acid residues at positions 11, 20, and 103 by any amino acid.

3. A purified variant of the protein having the amino acid sequence shown in SEQ ID NO:1, wherein said variant has anti-tumor activity in humans, and wherein said variant differs from the protein of SEQ ID NO:1 solely by substitution of the amino acid residue at position 11 with Val or Ile, the amino acid residue at position 20 with Asn or Asp, and the amino acid residue at position 103 with Arg or Ser.

4. A method of producing a protein with anti-tumor activity in humans comprising the following steps:

(a) homogenizing eggs from *Rana pipiens* in the presence of a weakly acidic buffer;

(b) subjecting the homogenized eggs to a first stage of cation exchange chromatography, wherein said protein remains bound to said cation exchange chromatograph and is subsequently eluted with about 0.1M salt;

(c) subjecting the eluant from step (b) to a second stage of cation exchange chromatography, wherein said protein remains bound to said cation exchange chromatograph and is subsequently eluted with about 0.1M salt; and (d) subjecting the eluant from step (c) to size exclusion chromatography and collecting proteins with apparent molecular weights of about 14 kDa to 16 kDa, thereby producing said protein.

5. A method of producing a protein with anti-tumor activity in humans comprising the following steps:

(a) homogenizing eggs from *Rana pipiens* in the presence of a weakly acidic buffer;

(b) subjecting the processed eggs to a first stage of cation exchange chromatography, wherein said protein remains bound to said cation exchange chromatograph in the presence of about 0.15M salt is eluted using a salt concentration that does not exceed 0.45M; and (c) subjecting the eluant from step (b) to size exclusion chromatography and collecting proteins with apparent molecular weights of about 14 kDa to 16 kDa, thereby producing said protein.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 104 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: N ( i v ) ANTI-SENSE: N ( v ) FRAGMENT TYPE: N-terminal ( v i ) ORIGINAL SOURCE:
    ( A ) ORGANISM: Rana pipiens
    ( D ) DEVELOPMENTAL STAGE: Oocyte ( x i ) SEQUENCE DESCRIPTION: SEQ ID NO:1:

```
Glu  Asp  Trp  Leu  Thr  Phe  Gln  Lys  Lys  His  Ile  Thr  Asn  Thr  Arg  Asp
1                  5                        10                       15

Val  Asp  Cys  Asp  Asn  Ile  Met  Ser  Thr  Asn  Leu  Phe  His  Cys  Lys  Asp
              20                       25                       30

Lys  Asn  Thr  Phe  Ile  Tyr  Ser  Arg  Pro  Glu  Pro  Val  Lys  Ala  Ile  Cys
         35                            40                  45

Lys  Gly  Ile  Ile  Ala  Ser  Lys  Asn  Val  Leu  Thr  Thr  Ser  Glu  Phe  Tyr
      50                       55                  60

Leu  Ser  Asp  Cys  Asn  Val  Thr  Ser  Arg  Pro  Cys  Lys  Tyr  Lys  Leu  Lys
65                       70                  75                            80

Lys  Ser  Thr  Asn  Lys  Phe  Cys  Val  Thr  Cys  Glu  Asn  Gln  Ala  Pro  Val
                   85                       90                  95

His  Phe  Val  Gly  Val  Gly  Ser  Cys
              100
```

( 2 ) INFORMATION FOR SEQ ID NO:2:

( i ) SEQUENCE CHARACTERISTICS:
    ( A ) LENGTH: 104 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: N ( i v ) ANTI-SENSE: N ( v ) FRAGMENT TYPE: N-terminal ( v i ) ORIGINAL SOURCE:
    ( A ) ORGANISM: Rana pipiens
    ( D ) DEVELOPMENTAL STAGE: Oocyte ( x i ) SEQUENCE DESCRIPTION: SEQ ID NO:2:

```
Glu  Asp  Trp  Leu  Thr  Phe  Gln  Lys  Lys  His  Val  Thr  Asn  Thr  Arg  Asp
1                  5                        10                       15

Val  Asp  Cys  Asn  Asn  Ile  Met  Ser  Thr  Asn  Leu  Phe  His  Cys  Lys  Asp
              20                       25                       30

Lys  Asn  Thr  Phe  Ile  Tyr  Ser  Arg  Pro  Glu  Pro  Val  Lys  Ala  Ile  Cys
         35                            40                  45

Lys  Gly  Ile  Ile  Ala  Ser  Lys  Asn  Val  Leu  Thr  Thr  Ser  Glu  Phe  Tyr
      50                       55                  60

Leu  Ser  Asp  Cys  Asn  Val  Thr  Ser  Arg  Pro  Cys  Lys  Tyr  Lys  Leu  Lys
65                       70                  75                            80
```

-continued

```
Lys  Ser  Thr  Asn  Lys  Phe  Cys  Val  Thr  Cys  Glu  Asn  Gln  Ala  Pro  Val
               85                       90                       95

His  Phe  Val  Gly  Val  Gly  Arg  Cys
               100
```